(12) United States Patent
Molino et al.

(10) Patent No.: US 7,147,612 B2
(45) Date of Patent: Dec. 12, 2006

(54) APPARATUS FOR CORRECTION OF LEG DEFORMITIES

(76) Inventors: Joseph L. Molino, 2 Aura Dr., Valley Cottage, NY (US) 10989; Micheal Rebarber, 28 Buckingham Pl., Glen Rock, NJ (US) 07452

( * ) Notice: Subject to any disclaimer, the term of this patent is extended or adjusted under 35 U.S.C. 154(b) by 174 days.

(21) Appl. No.: 10/897,952

(22) Filed: Jul. 23, 2004

(65) Prior Publication Data

US 2005/0038366 A1 Feb. 17, 2005

Related U.S. Application Data

(60) Provisional application No. 60/495,351, filed on Aug. 15, 2003.

(51) Int. Cl.
*A61F 5/00* (2006.01)
*A61F 5/37* (2006.01)

(52) U.S. Cl. .............................. 602/26; 602/5; 602/23; 128/882

(58) Field of Classification Search ................ 602/5, 602/16, 23, 25–26; 128/882
See application file for complete search history.

(56) References Cited

U.S. PATENT DOCUMENTS

| | | | |
|---|---|---|---|
| 4,691,698 A | | 9/1987 | Bremer |
| 4,772,286 A | * | 9/1988 | Goble et al. ............. 623/13.14 |
| 4,940,045 A | | 7/1990 | Cromartie |
| 5,697,893 A | * | 12/1997 | Rhenter ........................ 602/27 |
| 6,010,474 A | * | 1/2000 | Wycoki ........................ 602/23 |
| 6,090,057 A | * | 7/2000 | Collins et al. ................ 602/16 |
| 2003/0100853 A1 | * | 5/2003 | Yamasaki et al. ............. 602/16 |
| 2004/0059270 A1 | * | 3/2004 | Berretta ........................ 602/26 |
| 2004/0267179 A1 | * | 12/2004 | Lerman ........................ 602/26 |
| 2005/0004499 A1 | * | 1/2005 | Bauerfeind et al. ........... 602/26 |
| 2005/0240135 A1 | * | 10/2005 | Hoffmeier et al. ............ 602/26 |
| 2006/0015047 A1 | * | 1/2006 | Besselink et al. ............. 602/16 |

FOREIGN PATENT DOCUMENTS

| | | |
|---|---|---|
| DE | 2239382 | 2/1974 |
| EP | 0589663 | 3/1994 |

* cited by examiner

*Primary Examiner*—Henry Bennett
*Assistant Examiner*—Kari Petrik
(74) *Attorney, Agent, or Firm*—Lawrence G. Fridman (57) ABSTRACT

An orthotic device is formed with a stationary proximal receiving element adapted to receive at least a portion of a thigh region of a human limb and a distal receiving element adapted to receive a lower region of the human limb. The distal receiving element is pivotally movable with respect to the proximal receiving element by forces applied to a proximal region of the distal receiving element.

16 Claims, 7 Drawing Sheets

APPARATUS FOR CORRECTION OF LEG DEFORMITIES

This non-provisional application claims priority under 35 USC 119(e) of U.S. Provisional Application Ser. No. 60/495,351 filed by Joseph L. Molino and Michael Rebarber, on Aug. 15, 2003.

FIELD OF THE INVENTION

The present invention relates generally to medical devices, and more specifically, it relates to an orthotic device for correction of leg deformities.

BACKGROUND OF THE INVENTION

Blount's disease is a progressive disease that affects the varus angle of the tibia in children that is correctable with proper treatment. This disease is a progressive developmental condition that is characterized by disordered endochondral ossification of the medial tibial physis. This results in an abrupt varus deformity in the proximal tibia and is also associated with an internal torsion of the tibia. Current treatment of Blount's disease includes use of static orthotic devices or surgical procedure also known as tibial osteotomy. These procedures can create other misalignments, are incremental, and unnecessarily slow.

There are two forms of Blount's disease recognized. First is an infantile form of the disease which occurs prior to three years of age. Second is an adolescent form which occurs after age eight. Diagnostic characteristics of Blount's disease consist of: sharp varus angulations in the metaphysis, a widened and irregular physeal line medially, a medially sloped and irregularly ossified epiphysis, and a prominent beaking of the medial metaphysis, with lucent cartilage islands in the beak. Additional symptoms include pain, progressive bowing, an abnormal gait, and leg length discrepancies. The cause of Blount's disease is currently unknown.

The nature of Blount's Disease is in the bowing of the tibial portion of the leg and is based on the diminished growth capacity of the medial area of the tibia and a continued normal growth emanating from the lateral area of the tibia. This condition results in the normal growth of the lateral portion of the tibia, while growth of the medial portion of the tibial shaft is suppressed. The abnormality exists due to the continued growth of the lateral epiphysis and the stunted growth of the medial epiphysis causing a curving of the leg. This causes the outward bowing of the tibia which usually occurs in infants and is most prominent just after they start walking.

Currently, the disease is treatable by application of conventional braces with limited success and an unnecessarily long treatment period. The known prior art devices utilized for the correction of the tibia are very restrictive in nature and are typically utilized when the leg of a patient is in a straight position. The conventional medical devices utilized for treatment of Blount's disease are based on the application of a three point pressure system. The typical application of the three point pressure system is as follows: (1) the proximal most portion of the brace is adapted to produce a counter force at the upper portion of the inner femur; (2) the most distal portion of the brace generates a counter force at the ankle; and (3) the corrective pressure is exerted by pressure from the lateral side towards the medial counter forces. Unfortunately, during application of the three point pressure system, deformation and correction occurs not only at the tibia, which needs to be corrected, but the compensatory deformation and correction of the bone structure also occurs at the femur, which does not need to be corrected. During this prior art procedure often a perfectly normal and healthy bone is involved in the corrective process by introducing forces that are typically unnecessarily adapted to bend and deform the femur. Review of the mechanics of Blount's disease conducted by the prior art devices leads to the conclusion that correction of the affected part, namely the tibia, is the primary concern in the treatment of patients and not the treatment of the femur. This is because the treatment of the femur introduces additional and undesired deformity to the child's limb.

Since it is known that Blount's disease occurs typically with weight-bearing, bracing devices and methods adapted for treatment of this disease should be effective throughout all phases of the patient's activity. To minimize the progression of Blount's disease, the epiphyseal plate of the tibia needs to be aligned correctly while ambulating. Then the tibia will correct itself, as shown in the prior art study.

Thus, there has been a long felt and unsolved need for a medical device and procedure adapted for treatment of Blount's disease and capable of overcoming the shortcomings of the prior art. Specifically, there has been a need for a medical device which is capable of isolating the corrective forces and directing them for treatment of the distal portion of the leg or treating the tibial bone without affecting the Femur bone or stretching the medial collateral ligament (which is attached to the femur and to the tibia and is responsible for holding the knee joint together in the Coronal plane on the medial side of the leg).

SUMMARY OF THE INVENTION

In the device of the invention, a focused, dynamic force is applied to the tibia so as to generate the required correction. Such focused application of the corrective forces does not introduce deforming forces to the unaffected portions of the limb. The corrective forces are specifically directed at the area of the varus malformation, while not affecting the femur, the medial collateral ligament, the distal tibia or ankle complex.

To maintain the correct orientation of the ankle complex, an ankle joint is utilized which is substantially rigid in the proximal to distal direction and having substantial flexibility in the Coronal and Sagital planes. This allows the knee axis and ankle axis to remain in a neutral orientation while the required corrective forces are being applied.

The dynamic portion of the orthotic device of the invention is associated with the distal receiving element which is pivotal in the Coronal plane about an axis at the level of the varus deformity. This allows the corrective force is directed at the precise area of deformity without exerting pressure that could cause secondary deformities.

One aspect of the invention provides an orthotic device having a proximal receiving element adapted to receive at least a portion of a thigh area of a human limb in such a manner that the proximal receiving element is stationary with respect to the thigh region. Distal receiving element is adapted to receive at least a portion of a lower area of the human limb. The distal receiving element is formed with at least proximal and distal regions thereof spaced from each other. The distal receiving element with the portion of the lower area of the limb is pivotally movable with respect to the proximal receiving element by forces applied at the proximal region of the distal receiving element.

As to a further aspect of the invention, a proximal connecting element is associated with the proximal receiving element, a distal connecting element is associated with the distal receiving element and a knee joint is interposed between there. An adjustment member is movable along the distal connecting element and a medial connector extends outwardly from the adjustment member, so as to be associated with the distal receiving element. The adjustment member can be fixedly attached at a predetermined location on the distal connecting element, whereas a pivotal connection is provided between the medial connector and the distal receiving element.

As to another aspect of the invention, the pivotal forces applied to the proximal region of the distal receiving element are generated by a resilient connective element extending between the distal connecting element and the proximal region of the distal receiving element.

As to still another aspect of the invention, the orthotic device includes a foot supporting arrangement adapted to receive at least a portion of a foot of the human limb and an ankle joint which extends between the distal region of the distal receiving element and the foot supporting element. The ankle joint is substantially rigid in the proximal to distal direction and is substantially flexible in the Sagital and Coronal planes.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

DESCRIPTION OF THE PREFERRED EMBODIMENT

Referring now more specifically to FIGS. 1–8 of the drawings of the application. An orthotic device or apparatus 10 of the invention consists of a proximal cuff or proximal receiving element 12 adapted to receive an upper thigh area and a distal tibial cuff or distal receiving element 14 adapted to receive a lower leg area or a calf of a human limb. An ankle joint 16 is provided between the distal receiving element 14 and a foot supporting arrangement 18 adapted to receive a foot of a patient On the medial side the proximal receiving element 12 is attached by a proximal strut or proximal connecting element 20 to one side of a knee joint 22. A distal strut or distal connecting element 24 extends from another side of the knee joint 22 and is adapted for connection to the distal receiving element 14. This design requires only a single proximal connecting element 20 associated with the medial side of the proximal receiving element 12 and a single distal connecting element 24 associated with the medial side of the distal receiving element 14.

The proximal cuff of receiving element 12 and distal cuff of receiving element 14 are each formed from a semi-resilient material having a front opening adapted to facilitate insertion of the respective leg portion into the interior area thereof. The distal receiving element 14 can be formed with an extension 15 extending outwardly from the proximal region thereof and adapted for better engagement with an adjustable elastic corrective element 35.

In one embodiment of the invention, the proximal receiving element 12 is adapted to receive the thigh region of the leg from an area just below the greater trochanter on the lateral side, to approximately one inch distal to the perineum on the medial side. The distal region 21 of the proximal receiving element 12 extends to an area just above the medial and lateral femoral chondyles of the femur. The distal receiving element 14 is formed with a proximal 27 region which in this embodiment terminates well above the fibula neck. Reliefs are provided within the inner area of the element 14 to avoid or minimize contact with the fibula neck and fibula head. This is necessary to avoid impingement of the sensitive areas of the peroneal nerve and fibula head. In the same embodiment, the distal region 29 of the element 14 terminates just below the midpoint of the gastroc-solieus complex.

An ankle joint 16 extends outwardly from a medial part of the distal region 29 of the distal receiving element 14 so as to be connected to the proximal region 31 of the foot supporting element 18. The distal receiving element 14 is formed with hook and loop straps and chafes for closure.

An adjustment sub-assembly 37 consisting of an adjustment member 26, a medial connector 25 and pivotal arrangement 28 is provided for adjustment of positioning of the distal receiving element 14 and foot supporting element 18 connected thereto with respect to at least the distal connecting element 24. As illustrated by the arrow in FIG. 4, the adjustment member 26 is adapted for a longitudinal movement along the distal connecting element 24. In this manner its position can be adjusted and fixed by any conventional means, at any desirable location below the knee joint 22 on the distal connecting element 24. This enables the invention to adapt the brace to the conditions of individual patients.

Figure 1:
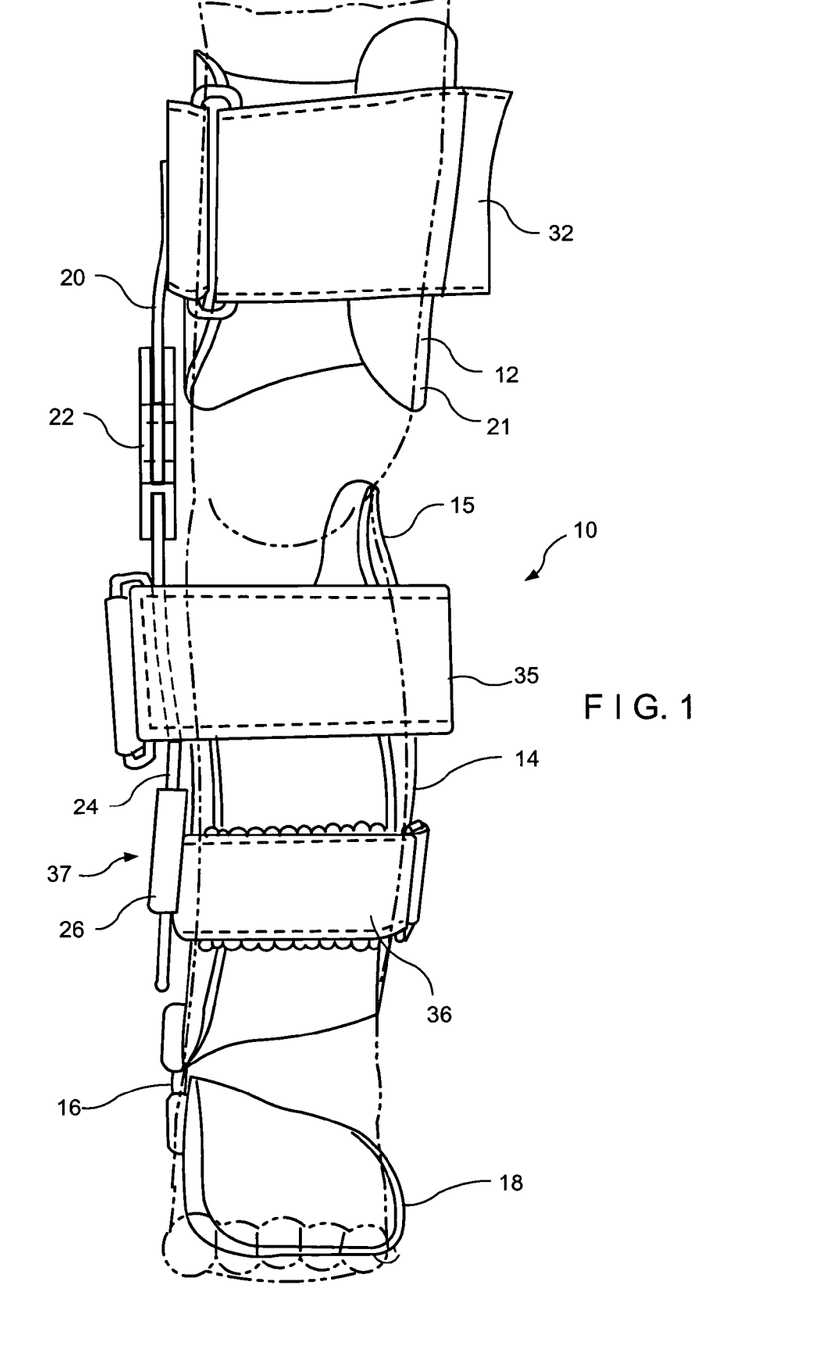
FIG. 1 is a front or anterior elevational view of the prosthetic device of the invention.
Figure 2:
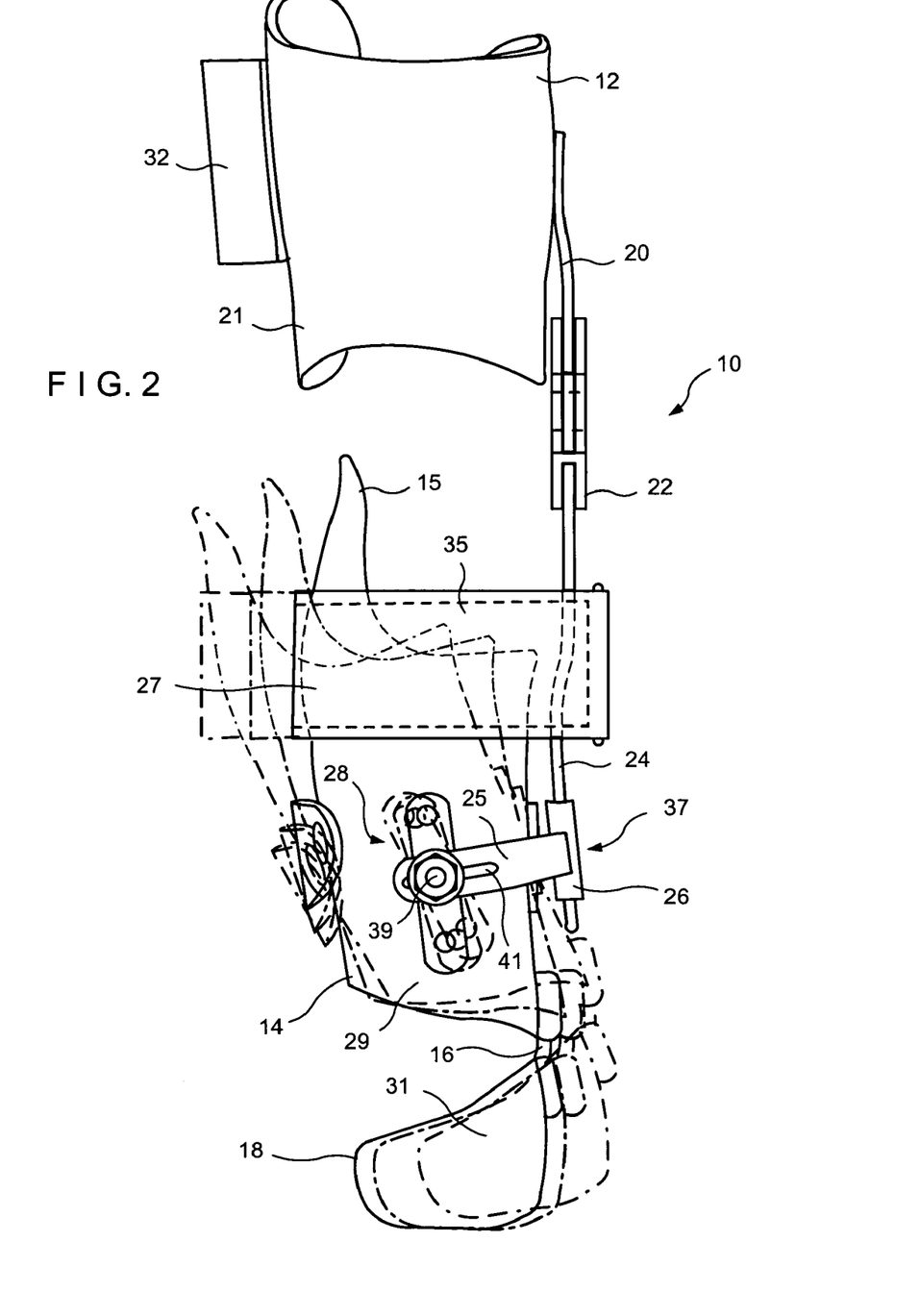
FIG. 2 is a rear or posterior elevational view thereof.
Figure 3:
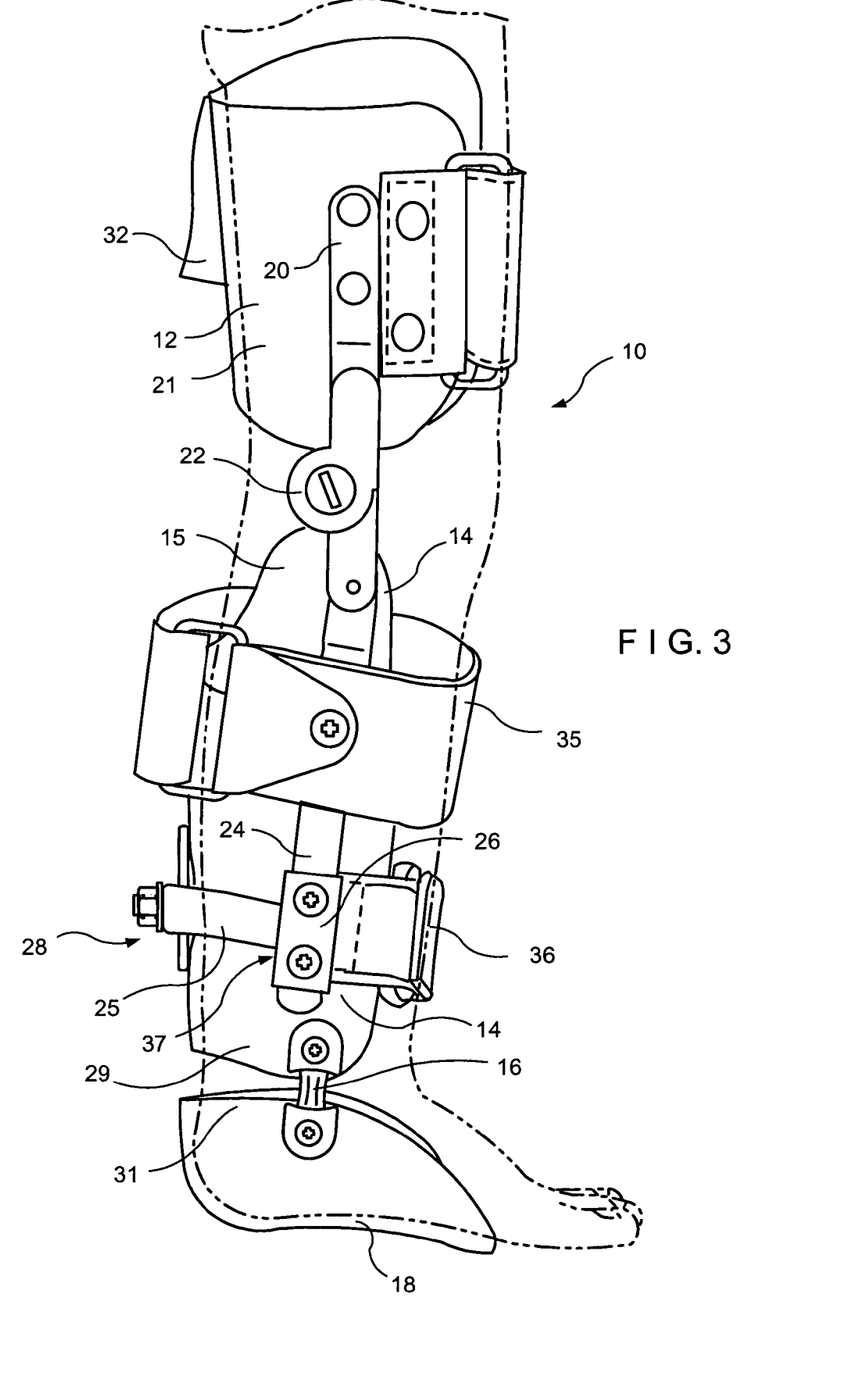
FIG. 3 is a medial side elevational view thereof.
Figure 4:
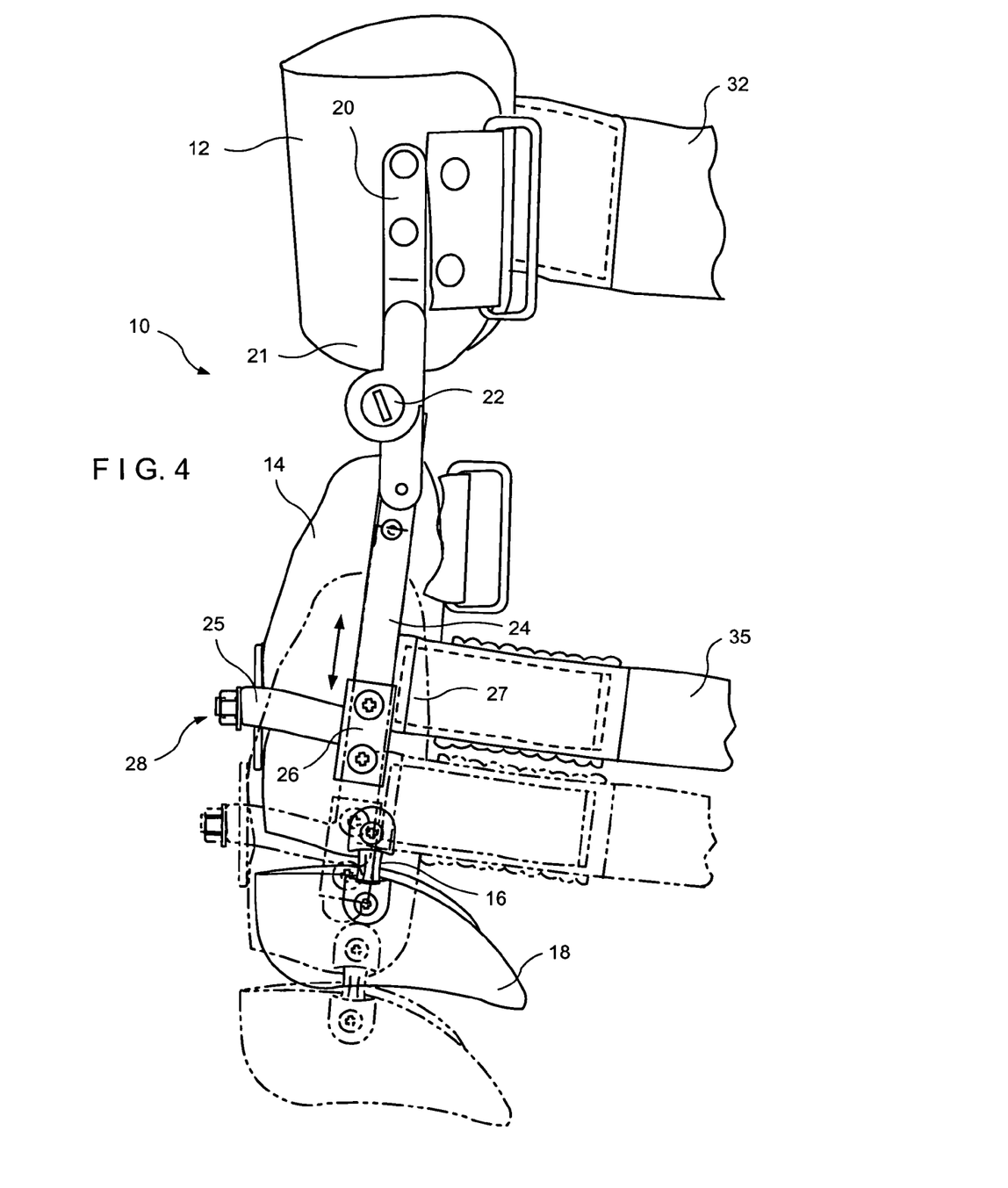
FIG. 4 is another medial side elevational view of the brace of the invention.
Figure 5:
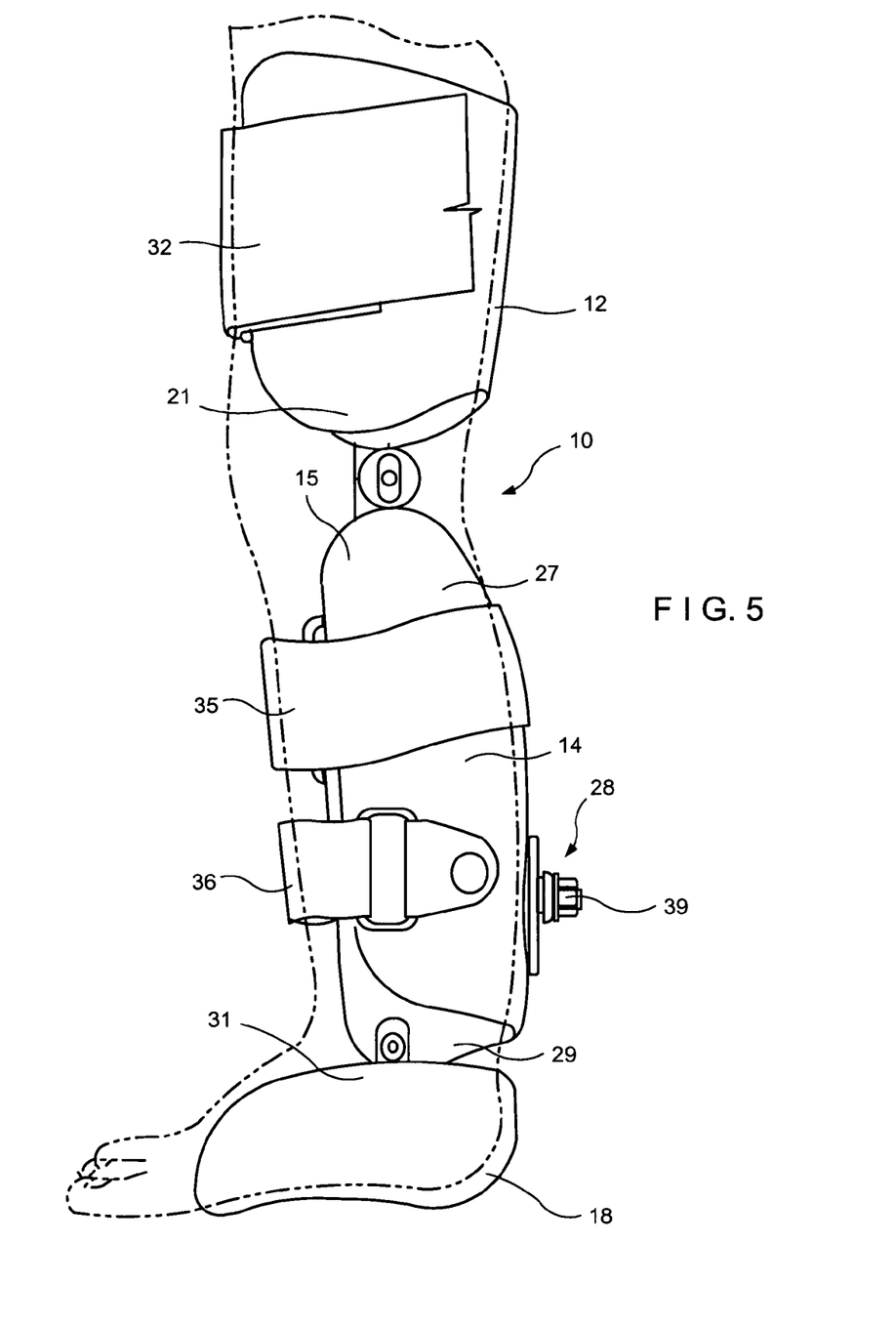
FIG. 5 is a lateral side elevational view thereof.

A medial connector 25 is interposed between the adjustment member 26 and the pivotal arrangement 28 which is associated with the distal receiving element 14. As best illustrated in FIGS. 2 and 9 the medial connector 25 extends from the adjustment member 26 in the Sagital plane curving gradually at approximately 90° angle, so as to be pivotally connected to the posterior region of the distal receiving element 14 in the Coronal plane at the pivotal arrangement 28. In other words, as best illustrated by at least FIGS. 4, 6 and 7 the connector 25 extends rearwardly and normally from the adjustment member 26 and then gradually changes in the direction toward the posterior portion of the distal receiving element 14.

The pivotal arrangement 28 typically includes a pivotal member 39 provided at an area of attachment of the medial connector 25 to the distal receiving element 14 in the Coronal plane. The Coronal plane is known to be a vertical plane extending from side to side that divides the body into front and back portions thereof. The pivotal arrangement 28, in general, and the pivotal member 39, specifically, has a subjective location depending upon patient's physiology. In the preferred embodiment, the pivotal member 39 is positioned on a posterior or rear surface of the distal receiving element 14 in the area corresponding to the location of the apex of the Gastroc Soleus Complex of a leg of a patient. In other words, the location of the pivotal member of the distal receiving element 14 may vary from patient to patient and is typically positioned at the location corresponding to the summit of the belly of the muscle on the back of the patient's leg.

Since, as best illustrated in at least FIGS. 2 and 9, the pivotal member 39 is attached to the posterior region of the distal receiving element 14 in the Coronal plane, the distal receiving element 14 is capable of moving or pivoting substantially in the same Coronal plane. This means that the element 14 pivots from the lateral to medial direction and vice versa relative to the distal connecting element 24. This occurs while the proximal receiving element 12 remains stationary. Position of the medial connector 25 and the connecting elements 20,24 relative to the pivotal member 39 also can be adjusted by means of a slot 41 formed in the connector 25.

Figure 6:
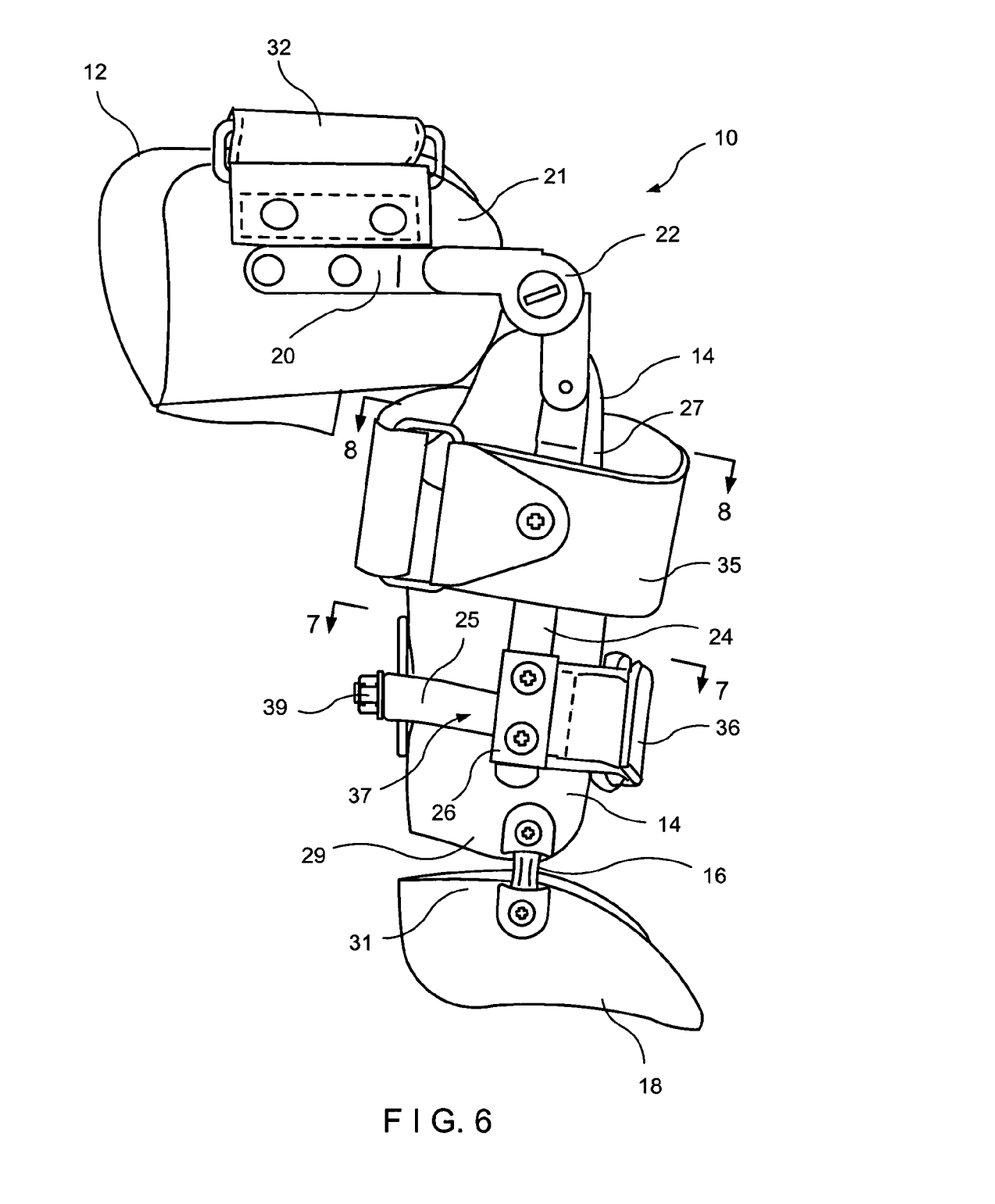
FIG. 6 is a side elevational view illustrating operation of a knee joint.
Figures 7, 8, 9:
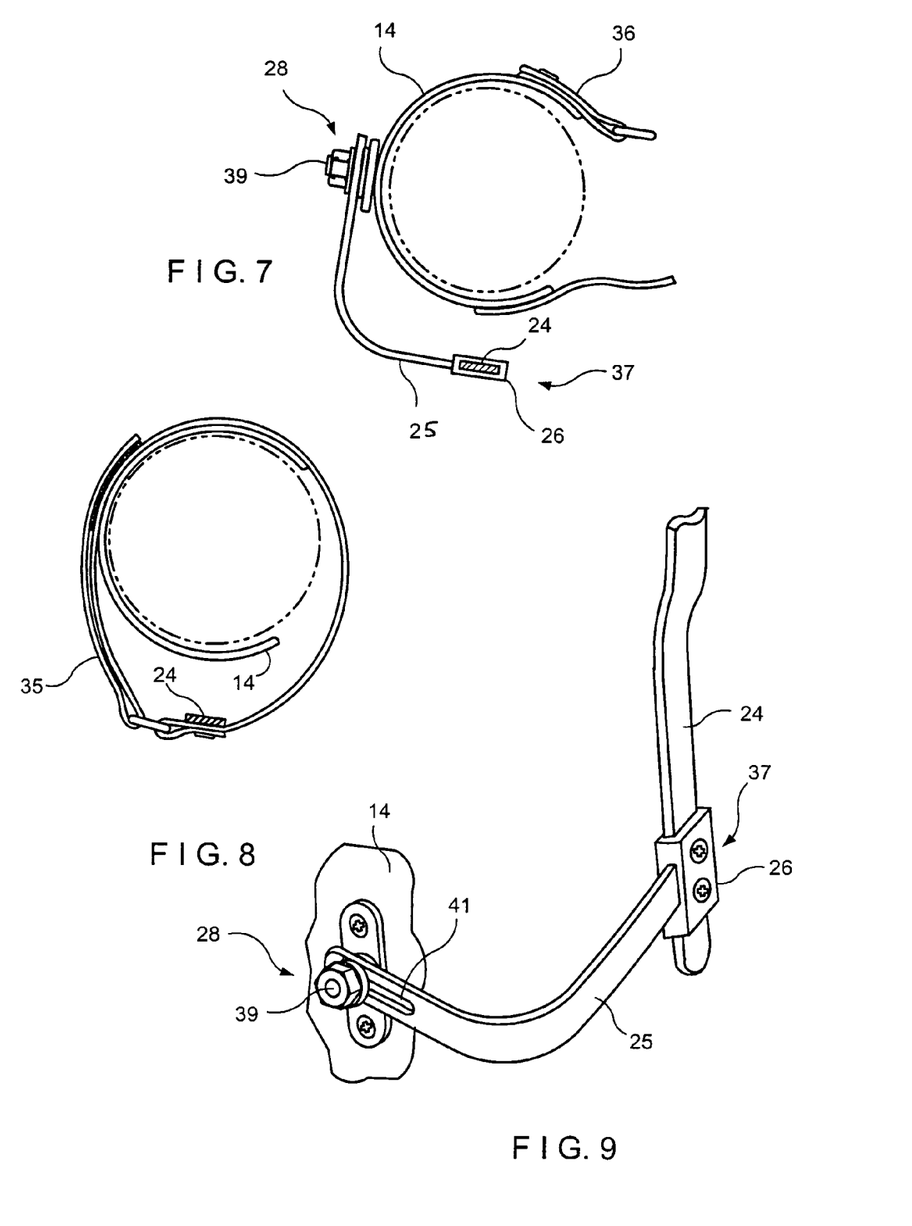
FIG. 7 is a sectional view according to sectional plane 7—7 of FIG. 6.
FIG. 8 is a sectional view according to sectional plane 8—8 of FIG. 6.
FIG. 9 is a partial view showing an adjustment sub-assembly in combination with a pivotal arrangement of the invention.

As best illustrated in FIG. 6, significantly, the knee joint 22 is isolated from and operates independently of the pivotal arrangement 28, so that the knee can flex and move throughout a substantial range of motion independently of the pivoting mechanism, so as to allow a patient to ambulate normally. This is one of the important aspects of the invention that is essential for proper correction of the curvature of the tibia caused by Blount's disease without having a patient subjected to locked knee.

To enhance flexibility of the orthotic device 10, the ankle joint or extension 16 is provided on the medial side extending between the distal region 29 of the distal or tibial receiving element 14 and the proximal region 31 of the foot supporting element 18. The ankle joint 16 is substantially rigid in the proximal to distal direction, but has sufficient flexibility in the Coronal and Sagital planes. The Sagittal plane is known to be an anterior-posterior vertical plane passing through the body from front to back, dividing the body in half.

On the lateral side, the foot supporting element 18 is allowed to move substantially unrestricted with respect to the distal receiving element 14. The receiving element 14—ankle joint 16—foot supporting element 18 interface is necessary to insure that the orthotic device 10 does not migrate distally. In this manner all hinge surfaces are kept congruent to the actual knee axis and ankle axis. Therefore, when a predetermined position of the adjustment member 26 is reached and it is fixedly attached to the distal connecting element 24, the distances between the axis of the knee joint 22, the longitudinal axis of the medial connector 25, and the axis of the foot supporting element 18 (including the axis of the ankle joint 16) remain virtually unchanged during the treatment.

When the distal receiving element 14 is allowed to move in the pivotal fashion at the pivotal arrangement 28, such movement does not affect orientation of the bottom of the foot situated in the foot supporting element 18 with respect to the ground surface. One of the main functions of the foot supporting element 18 and the ankle joint 16 is to keep all major elements of the orthotic device 10 at the predetermined elevation or height with respect to the ground. This prevents undesirable distal migration of the elements of the device. In this manner, the knee hinge 22 and the knee center are constantly positioned within the same plane of flexion and proper height to insure a proper location of the center of rotation.

In view of the resiliency of the ankle joint 16 in the Coronal and Sagital planes, as the distal receiving element 14 pivots inward and outward, the foot of a patient situated in the foot supporting element 18 is allowed to substantially engage or contact the ground. This occurs throughout the pivotal motion of the distal receiving element 14 and throughout the entire dynamics of the gait pattern. Thus, as dynamic correction is exerted on the proximal portion of the tibia, the foot is allowed to flatly engage the floor.

There is typically at least one proximal holding non-elastic element or a strap 32 associated with the proximal receiving element 12, and at least one distal holding non-elastic element or a strap 36 associated with the distal receiving element 14. The proximal holding element 32 is adapted to hold the thigh portion of the leg within confinement of an interior area of the proximal receiving element 12. On the other hand, the distal holding element 36 is provided for holding the calf area of the same leg within the confinement of the interior area of the distal receiving element 14. It should be also understood that any reasonable number of such holding elements can be associated with any receiving element or adapted to hold the respective portion of the human limb within the corresponding receiving element.

As illustrated in FIGS. 1–6, the straps are connected to the respective receiving elements by means of chafes and are formed with tightening/fixing elements in the form of hook and loop connectors also known as VELCRO® fasteners. Although, the specific way of connection between the straps and the receiving element has been disclosed, it should be understood that any conventional way of attachment/connection between the straps and the receiving element is within the scope of the invention.

A corrective or torsional elastic element 35 is associated with the proximal region of the distal receiving element 14 so as to surround the distal connecting element 24 in the area between the knee joint 22 and the adjustment member 26. According to the invention, through tightening manipulation of the elastic or torsional element 35, varying pressure is applied on the distal receiving element 14 as needed to facilitate application of the medially directed corrective forces to the deformed limb.

Upon tightening, the corrective elastic strap 35 (see FIG. 2) is capable of exerting the medially or inwardly directed pressure which causes the proximal region of the distal receiving element 14 and the lower portion of the limb situated thereinside to move or tilt inwardly and the distal region thereof to move or tilt outwardly. Actually, the action of the elastic corrective element 35 causes an inwardly directed force that pulls the distal receiving element 14 and the lower portion of the limb situated thereinside in the medial direction. As the distal receiving element 14 is tilted, the foot supporting element 18 retains its engagement with the floor.

As illustrated on FIGS. 1–4, the corrective strap 35 is positioned around the proximal region 27 of the distal receiving element 14. Then in a conventional fashion it can be hooked through a chafe and brought back and fastened. The pressure exerted by corrective element 35 can be adjusted by any conventional means, such as a friction buckle, etc. The combination of the pivotal arrangement 28 and the corrective resilient element 35 negates the necessity of using a three point pressure system of the prior art, which, as discussed hereinabove, adversely affects the femur and places undue stresses on the bone which does not need to be corrected. The orthotic device of the invention specifically directs the majority of the corrective forces only to the tibia.

The application of the corrective resilient element 35 to the proximal region 27 of the distal receiving element 14 provides the dynamic force in the orthotic device of the invention specifically directed at the level of the varus deformity. This causes pivotal motion of the distal receiving element 14 in the Coronal plane and generates the corrective force directed at the precise area of deformity without exerting unnecessary forces that are capable of causing ancillary damage to the femur or distal tibia and/or medial collateral ligament.

As indicated hereinabove, the prior art medical devices must be worn when the leg is straight. Therefore, if a patient is ambulatory he must walk with a locked knee and with a stiff leg. Therefore, the prior art braces are typically worn while patients are sleeping or ambulate unnaturally with great difficulty. The dynamic nature of the present invention allows the patient to have a normal life activity. This is because flexion of the knee, facilitated by the knee joint 22, does not affect the corrective forces that are placed on the affected area or the tibia.

The orthotic device 10 of the invention is dynamic in nature and does not rely on significant counter pressure at the proximal femur. Thus, correction of the leg deformity is taking place even when the limb is not in full extension. This allows correction to occur while the patient is ambulatory or resting and though the entire range of motion of the lower limb. Such arrangement increases the wearing time of the orthosis on a daily basis and thereby effecting a change in a shorter time period, which will reduce the total time needed to correct the varus.

As discussed hereinabove, the invention is primarily adapted to correct the curvature of the tibial bone caused by the Blount's disease in infants by the nature of the forces exerted by this device. It should be noted however, that the brace of the invention can be also be used to treat other medical conditions. For example, it can be used to correct Medial Compartment Syndrome caused by arthritic changes in the medial compartment between the femur and the tibia at the knee joint. Medial Compartment Syndrome is such that the cartilage of both the tibia and femur are worn away. More specifically, the arthritic changes are that the condyal surfaces of the cartilage in the medial compartment of the knee are worn away, and that rough bony surfaces are allowed to contact each other, causing excruciating pain and further degeneration of the medial portion of the knee joint. By eliminating the stresses and opening up the medial compartment, so that these areas are not allowed to rub against each other. This apparatus and method of the invention minimize pain and cause a person to become more functional. And the nature of this device lends itself to treatment of that specific situation.

What is claimed is:

1. An orthotic medical device, comprising:
a proximal receiving element adapted to receive at least a portion of an upper area of a human limb, said proximal receiving element being substantially stationary with respect to said upper limb area;
a distal receiving element adapted to receive at least a portion of a lower area of said human limb, said distal receiving element having at least proximal and distal regions spaced from each other, said distal receiving element with said at least a portion of the lower limb area being pivotally movable with respect to said proximal receiving element by forces applied at said proximal region of said distal receiving element;
a proximal connecting element associated with said proximal receiving element, a distal connecting element associated with said distal receiving element, and a knee joint interposed between said proximal and distal connecting elements; and
an adjustable member movable along said distal connecting element, a medial connector extending outwardly from said adjustable member, so as to be associated with said distal receiving element and facilitate movement of said distal receiving element along said distal connecting element.

2. The orthotic device according to claim 1, wherein said adjustable member can be fixedly attached at a predetermined location on said distal connecting element and a pivotal connection is provided between said medial connector and said distal receiving element.

3. The orthotic device according to claim 2, wherein said pivotal forces are applied to the proximal region of the distal receiving element by a resilient corrective element extending between the distal connecting element and the proximal region of the distal receiving element.

4. The orthotic device according to claim 2, wherein said medial connector extends from said adjustable member in the Sagital plane curving gradually so as to be attached to the posterior region of the distal receiving element in the Coronal plane.

5. The orthotic device according to claim 4, wherein said pivotal member providing pivotal connection between said medial connector and said distal receiving element is situated within the Coronal plane and said medial connector curves approximately at 90° angle between said Sagital and Coronal planes.

6. The orthotic device according to claim 5, wherein the distal receiving element pivots with respect to the distal connecting element in the Coronal plane from lateral to medial direction and vice versa.

7. The orthotic device according to claim 1, further comprising a foot supporting arrangement adapted to receive at least a portion of a foot of said human limb and an ankle joint extending between said distal region of the distal receiving element and said foot supporting arrangement.

8. The orthotic device according to claim 7, wherein said ankle joint is substantially rigid in the proximal to distal direction and is substantially flexible in the Coronal and Sagital planes.

9. The orthotic device according to claim 8, wherein the pivotal motion of the distal receiving element and the portion of the lower limb area received thereinside does not affect orientation of the bottom of the foot situated within the foot supporting arrangement with respect to the ground.

10. The orthotic device according to claim 1, further comprising at least one proximal non-elastic holding element adapted to hold said at least portion of the upper limb area within said proximal receiving element and at least one distal non-elastic holding element adapted to hold at least said portion of the lower limb area within said distal receiving element.

11. The orthotic device according to claim 1, wherein said proximal receiving element and said medial connector are fixedly positioned with respect to said knee joint.

12. An orthotic medical device for correction of Coronal plane leg deformities, comprising;
a proximal receiving element adapted to receive at least a portion of an upper area of a human limb; a distal receiving element adapted to receive at least a portion of a deformed lower area of said human limb, said distal receiving element having at least proximal and distal regions spaced from each other, a proximal connecting element associated with said proximal receiving element, a distal connecting element associated with said distal receiving element, and a knee joint interposed between said proximal and distal connecting element;

said distal receiving element with said at least a portion of the deformed lower area of the limb is pivotally movable with respect to said distal connecting element by forces applied at said proximal region of the distal receiving element; and an adjustable member movable along and capable of being fixedly attached at predetermined locations on said distal connecting elements, a medial connector extending outwardly from said adjustable member, so as to be associated with a pivotal arrangement provided between said medial connector and said distal receiving element.

13. The orthotic device according to claim 12, wherein said pivotal forces are applied to the proximal region of the distal receiving element and to the portion of the deformed lower area of the limb by a resilient corrective element extending between the distal connecting element and the proximal region of the distal receiving element.

14. The orthotic device according to claim 13, further comprising a foot supporting arrangement adapted to receive at least a portion of a foot of said human limb and an ankle joint extending on a medial side of said device between said distal region the distal receiving element and said foot supporting arrangement, said ankle joint being substantially rigid in the proximal to distal direction and having substantial flexibility in the Coronal and Sagital planes.

15. The orthotic device according to claim 14, wherein the pivotal motion of the distal receiving element and a portion of the deformed lower limb area received thereinside do not affect orientation of the bottom of the foot situated within the foot supporting arrangement with respect to the ground.

16. The orthotic device of claim 12, wherein said medial connector extends from said adjustment member and curves between said Sagital and Coronal planes.

* * * * *